United States Patent
Whitaker et al.

(10) Patent No.: US 7,427,267 B2
(45) Date of Patent: Sep. 23, 2008

(54) BLOOD PRESSURE DETERMINING METHOD

(75) Inventors: Tyson B. Whitaker, Arden, NC (US); Craig M. Meyerson, Syracuse, NY (US); Edward Wright, Raleigh, NC (US); Mark E. Pingel, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 114 days.

(21) Appl. No.: 11/369,049

(22) Filed: Mar. 6, 2006

(65) Prior Publication Data

US 2007/0208258 A1  Sep. 6, 2007

(51) Int. Cl.
*A61B 5/02* (2006.01)

(52) U.S. Cl. ...................................... 600/490

(58) Field of Classification Search ......... 600/490–503, 600/481, 485
See application file for complete search history.

(56) References Cited

U.S. PATENT DOCUMENTS

| | | | | |
|---|---|---|---|---|
| 3,039,044 A | * | 6/1962 | Dubsky et al. ............... 73/728 |
| 4,969,466 A | * | 11/1990 | Brooks ....................... 600/494 |
| 5,730,139 A | * | 3/1998 | Miyazaki et al. ............ 600/493 |
| 6,068,601 A | * | 5/2000 | Miyazaki et al. ............ 600/490 |
| 6,511,435 B1 | | 1/2003 | Bluth et al. |
| 6,520,918 B1 | | 2/2003 | Stergiopoulos et al. |
| 6,705,998 B2 | | 3/2004 | Stergiopoulos et al. |
| 6,805,671 B2 | | 10/2004 | Stergiopoulos et al. |
| 6,817,836 B2 | | 11/2004 | Nose et al. |
| 7,008,379 B2 | * | 3/2006 | Takahashi et al. ........... 600/490 |
| 7,104,960 B2 | * | 9/2006 | Takahashi et al. ........... 600/490 |
| 2004/0127801 A1 | | 7/2004 | Takahashi et al. |

* cited by examiner

*Primary Examiner*—Charles A. Marmor, II
*Assistant Examiner*—Navin Natnithithadha
(74) *Attorney, Agent, or Firm*—Hiscock & Barclay, LLP

(57) ABSTRACT

In blood pressure measurement of a vertebrate through use of an inflatable pressure cuff disposed about a limb of the vertebrate limb and inflated by pump driven by a motor, the air pressure within the cuff is determined at any given time during the inflation of the cuff by calculating the incremental change in pressure in the pressure cuff over a series of small time increments and summing the calculated incremental pressure changes from the initiation of cuff inflation to a desired point in time during the inflation of the pressure cuff. The incremental change in pressure within the cuff is calculated as a function of the incremental change in current drawn by the pump motor over the time increment.

7 Claims, 2 Drawing Sheets

BLOOD PRESSURE DETERMINING METHOD

FIELD OF THE INVENTION

This invention relates generally to the non-invasive measurement of blood pressure and, more particularly, to the measurement of blood pressure via a blood pressure apparatus equipped with a rotary pump.

BACKGROUND OF THE INVENTION

The measurement of blood pressure is a common procedure used in hospitals, clinics and physicians' offices as a tool to assist in diagnosis of illness and monitoring of sick patients, as well as an indicator of the general status of a person's health. In standard non-invasive blood pressure measurement practice, blood pressure is measured using an inflatable sleeve, commonly referred to as a cuff, to measure arterial blood pressure. The cuff, which is adapted to fit around a limb over an artery of a patient, typically around the patient's arm over the brachial artery, includes an interior chamber adapted to be inflated with air to provide a certain amount of pressure on the artery in the arm.

Electronic blood pressure measurement devices for automatically inflating the cuff and automatically sensing the blood pressure either during inflation of the cuff or during deflation of the cuff are well-known in the art. In such devices, a motor driven pump is operatively connected to the interior chamber of the cuff by means of a tube, commonly referred to as a lumen. Upon activation of the pump motor, air is pumped by the pump through the tube to inflate the interior chamber of the cuff to a pressure sufficient pressure on the artery to stop the blood flow through the artery. A bleed valve is also operatively connected in fluid communication with the interior chamber to permit depressuring of the interior chamber when it is desired to deflate the cuff, either step-wise or rapidly, as desired. Generally, a pressure sensing device, typically a pressure transducer, is operatively connected in fluid communication with the interior chamber of the cuff to directly sense the pressure within the interior chamber of the cuff.

Automated blood pressure measurement devices commonly employ either an auscultatory technique or an oscillometric technique to detect when the systolic blood pressure, which corresponds to the cessation of blood flow through the artery, is reached, and when the diastolic blood pressures, which corresponds to unrestricted blood flow through the artery, is reached. In a conventional auscultatory method, a sound sensing device, commonly a microphone, is provided in operative association with the cuff to listen for pulsating sounds, known as Korotkoff sounds, associated with the flow of blood through an artery under pressure. In a conventional oscillometric approach, one or more pressure sensing devices, for example pressure transducers, are provided in operative association with the cuff to detect small oscillatory pressures that occur within the cuff as the result of the pulsating characteristic of blood flow through the artery.

Electronic circuitry, including a central processing unit, is provided that processes the signals from the sensors and determines the systolic and diastolic blood pressures. Typically, a digital display is also provided for displaying the systolic and diastolic blood pressures. Alternatively, the signals indicative of the systolic and diastolic blood pressure measurements may be transmitted to an external device, such as a laptop or a patient monitor, for display and/or data recording.

A detailed discussion and description of the operation of an exemplary embodiment of an electronic apparatus for the non-invasive measurement of blood pressure is presented in co-pending U.S. patent application Ser. No. 10/619,380, filed Jul. 14, 2003, subject to assignment to the common assignee of this application, and entitled "Motion Measurement In A Blood Pressure Measurement Device", and published Feb. 10, 2005, as Patent Application Publication No. US2005/0033188A1, which application is incorporated herein by reference.

Pressure transducers are analog devices, that is, the output signal from a pressure transducer is an analog signal. To be processed by the central processing unit, the analog signal must first be converted to a digital signal. To this end, conventional electronic blood pressure measurement devices include an analog-to-digital converter that functions to convert the analog signal from the pressure transducer to a digital signal for further processing.

Although such conventional prior art automatic blood pressure monitoring devices are effective, components such as pressure transducers and analog-to-digital converters are costly and complicate the devices. The need exists for a lower cost automatic pressure measurement device having fewer components or lower cost components.

SUMMARY OF THE INVENTION

It is a general object of the present invention to provide a method of determining blood pressure without directly measuring the pressure within a pressure cuff.

It is an object of an aspect of the invention to provide a method for determining blood pressure without using analog pressure transducer and analog-to-digital converter.

It is an object of an aspect of the invention to provide an apparatus for determining blood pressure without directly measuring the pressure within a pressure cuff.

In one aspect of the invention, a method is provided for determining blood pressure using an inflatable pressure cuff disposed about a vertebrate's limb by estimating the air pressure within the cuff as a function of motor torque. In an embodiment, the incremental change in pressure in the cuff is determined function of the incremental change in current drawn by the pump motor. At any point during the process of inflating the cuff, the pressure within the cuff is determined by summing the incremental pressure changes from initiation of cuff inflation to the desired point in time. The incremental change in current drawn by the pump motor is measured at least 40 times per second and advantageously between 100 to 200 times per second.

In one aspect of the invention, an apparatus is provided for determining blood pressure in operative association with an inflatable pressure cuff disposed about a vertebrate's limb. In an embodiment, the apparatus includes an air pump in fluid communication with the inflatable cuff, a direct current motor for driving the air pump, a current measurement device for measuring the current drawn by the motor, a controller for determining the incremental change in current drawn by the motor over a time increment, for estimating the corresponding incremental change in air pressure within the cuff, and for summing the estimated incremental changes in cuff pressure.

BRIEF DESCRIPTION OF THE DRAWINGS

For a further understanding of these and objects of the invention, reference will be made to the following detailed description of the invention which is to be read in connection with the accompanying drawing, where.

DETAILED DESCRIPTION OF THE INVENTION

Figure 1:
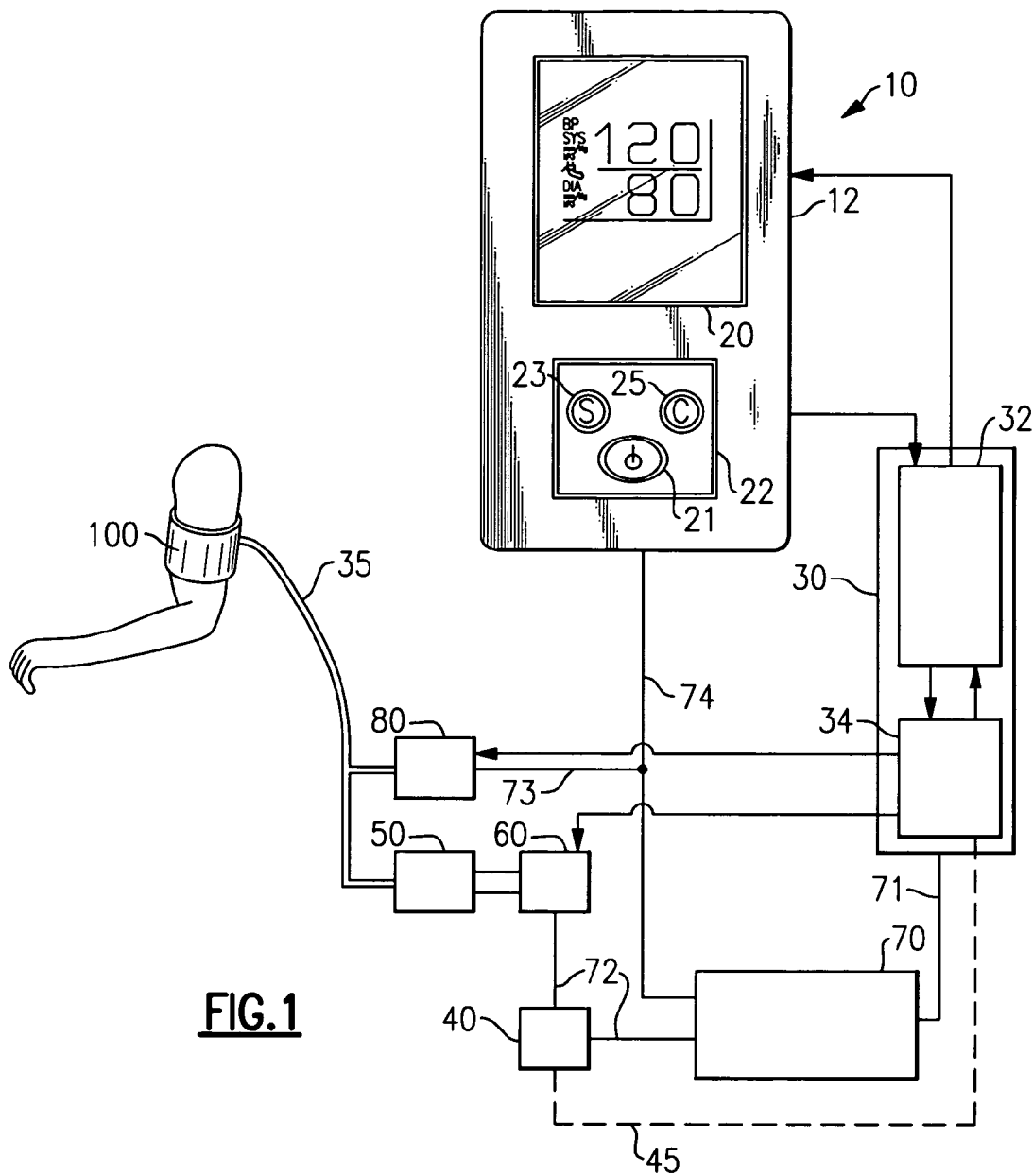
FIG. 1 is a schematic block diagram of an embodiment of a blood pressure measurement apparatus in accordance with the invention.

The present invention will be described herein with reference to an exemplary embodiment of a modular blood pressure measurement apparatus 10 depicted in FIG. 1. In the depicted embodiment, the blood pressure measurement apparatus 10 includes a display 20 and a user interface 22 operatively connected to a controller 30 that includes a central processing unit, "CPU", 32 and non-invasive blood pressure module, "NIBP", 34. The blood pressure measurement apparatus 10 further includes an air pump 50, a direct current motor 60, a power supply 70, such as rechargeable battery power pack, and a vent valve 80. The power supply 70 supplies power to the controller 30 through line 71, to the DC motor 60 through line 72, to the vent valve 80 through line 73 and to the display 20 and user interface 22 through line 74. The pump 50 and vent valve 80 are coupled in pneumatic communication in a conventional manner via a flexible conduit 35 to a blood pressure measurement cuff 100 applied to a limb of a vertebrate. The cuff 100 may be any conventional type of blood pressure measurement cuff, such as various "monitor" style cuffs available from Welch Allyn, Inc., headquartered in Skaneateles, N.Y., in sizes for thigh, large adult, adult, small adult, child, small child, and infant. The conduit 35, also commonly referred to as a lumen, may be a rubber tube or a conduit of other suitable material.

The display 20 includes a region for displaying information relating to a blood pressure measurement including the systolic blood pressure (SYS) and the diastolic blood pressure (DIA) measurements in either milligrams of Mercury ("mmHg") or Pascals ("kPa") or could also display mean pressure and heart rate. Both the systolic and diastolic blood pressures are displayed as a numeric two or three digit number. For purposes of illustration, the systolic and diastolic blood pressures are shown in FIG. 1 as 120 mmHg and 80 mmHg, respectively. The display 20 may be a LCD display as illustrated in the embodiment shown in the drawings.

The user interface 22 may include, for example, a plurality of input keys 21, 23 and 25. Key 21 is an on/off switch for selectively powering the apparatus 10 on and off. Key 23 is a start switch for selectively initiating a blood pressure measurement procedure and key 25 is stop switch for selectively canceling a blood pressure measurement procedure.

The controller 30 includes a control circuit including the CPU 32 and the NIBP module 34 on a printed circuit board 30 supported within the housing (not shown) of the apparatus 10. The CPU 32, for example a microprocessor, interacts with the display 20, the input keys 21, 23 and 25, and the NIPB module 34. The NIBP module 34, which may be a software module incorporated into the microprocessor 32 or may comprise a separate microprocessor coupled in communication with the microprocessor 32, controls operation of the pump 50, the DC motor 60 and the vent valve 80. The pump 50, which may be a rotary positive displacement pump or other type of inflation pump, is pneumatically coupled to the blood pressure cuff through conduit 35 and is operable to inflate blood pressure cuff 100 in response to a command signal from the NIBP module 34. The vent valve 80 is also pneumatically coupled to the blood pressure cuff 100 through the conduit 35 and provides for selective venting of air from the cuff 100 to deflate the cuff in response to a command signal from the control of the NIBP module 34.

As in conventional practice, to initiate a blood pressure measurement procedure, the user depresses the on/off switch key 21 to power up the various components of the blood pressure measurement apparatus 10. With the blood pressure measurement cuff 100 in place on the patient, the user depresses the start key 23 to initiate the blood pressure measurement procedure. In response, the microprocessor 32 activates the NIBP module 34 and the NIBP module sends a command signal to activate the DC motor 60 to drive the pump 50 to inflate the cuff 100. As the cuff 100 is inflated, the patient's diastolic and systolic blood pressures are determined, in accord with the invention, as a function of the incremental change in torque on the DC motor 60 driving the pump 50 as it inflates the cuff 100, rather than via direct measurement via a pressure transducer, or other pressure sensing device, of the air pressure within the interior chamber of the cuff 100.

For a particular motor design, the torque on the DC motor 60 driving the pump 50 may be determined at any point in the process of inflating the cuff 100 through measurement of the electric current drawn by the motor 60 at that instant in time. The incremental change, delta I, in the current drawn by the DC motor 60 over a time increment, delta t, is determined by measuring the current draw at time 1 and again at time 2 a desired period of time thereafter and applying the relationship:

$\Delta I = I_{t1} - I_{t2}$, where $\Delta I$ is the incremental current change over the time increment, $\Delta t$, equal to $t_2 - t_1$;

$I_{t1}$ is the measured current draw at time $t_2$; and $I_{t2}$ is the measured current draw at time $t_2$.

Since the torque on the DC motor 60 is reflective of the work being done by the motor, the cuff pressure at any point in the inflation process will be proportional to the torque on the motor at that time. Therefore, the incremental change in cuff pressure over an increment of time is proportional to the incremental change in current drawn by the motor 60 over that increment of time and can be calculated by the relationship:

$\Delta P = k_1 * \Delta I$, where $\Delta I$ is the incremental current change over the time increment, $\Delta t$, equal to $t_2 - t_1$;

$\Delta P$ is the incremental pressure change over the time increment, $\Delta t$, equal to $t_2 - t_1$; and $k_1$ is a conversion factor for converting motor current to pressure to be determined empirically for a particular motor design.

The cuff pressure at any point in the inflation process can be determined by summing the incremental pressure changes determined using the afore-presented formula for calculating the incremental pressure change, $\Delta P$, over the time increment, $\Delta t$. In practice, the incremental pressure change would be determined over very small time increments, for example $1/200^{th}$ to $1/100^{th}$ second.

Figure 2:
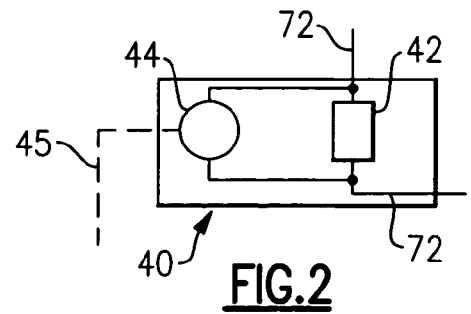
FIG. 2 is a schematic diagram of an exemplary embodiment of a motor current monitor.

In accord with one aspect of the invention, a current measurement device 40 is provided to measure the electric current drawn by the motor 60. As illustrated in FIG. 2, the current measurement device 40 may, for example, comprise an in-line resistor 42 of known resistance, disposed in the current supply line 72 between the power supply 70 and the DC motor 60, and associated electronic circuitry device 44 for monitoring the voltage drop across the resistor. At periodic time intervals, for example $1/200^{th}$ to $1/100^{th}$ second, the NIBP module 34 calculates the instantaneous current drawn by the DC motor 60 in a conventional manner using the measured voltage drop across the known resistance, and thence calculates the incremental change in current from the prior current measurement. The NIBP module 34 then calculates the incremental pressure change over the time increment based on the incremental change in current drawn by the motor 60 over that time increment. The NIBP module 34 continuously sums the incremental pressure changes from the initiation of inflation forward thereby providing the actual pressure in the cuff 100 at any point in time in the inflation process. Thus, in the method of the invention, the cuff pressure is known in real time at any point within the inflation process without actually sensing the pressure by means of a pressure transducer.

Figure 3:
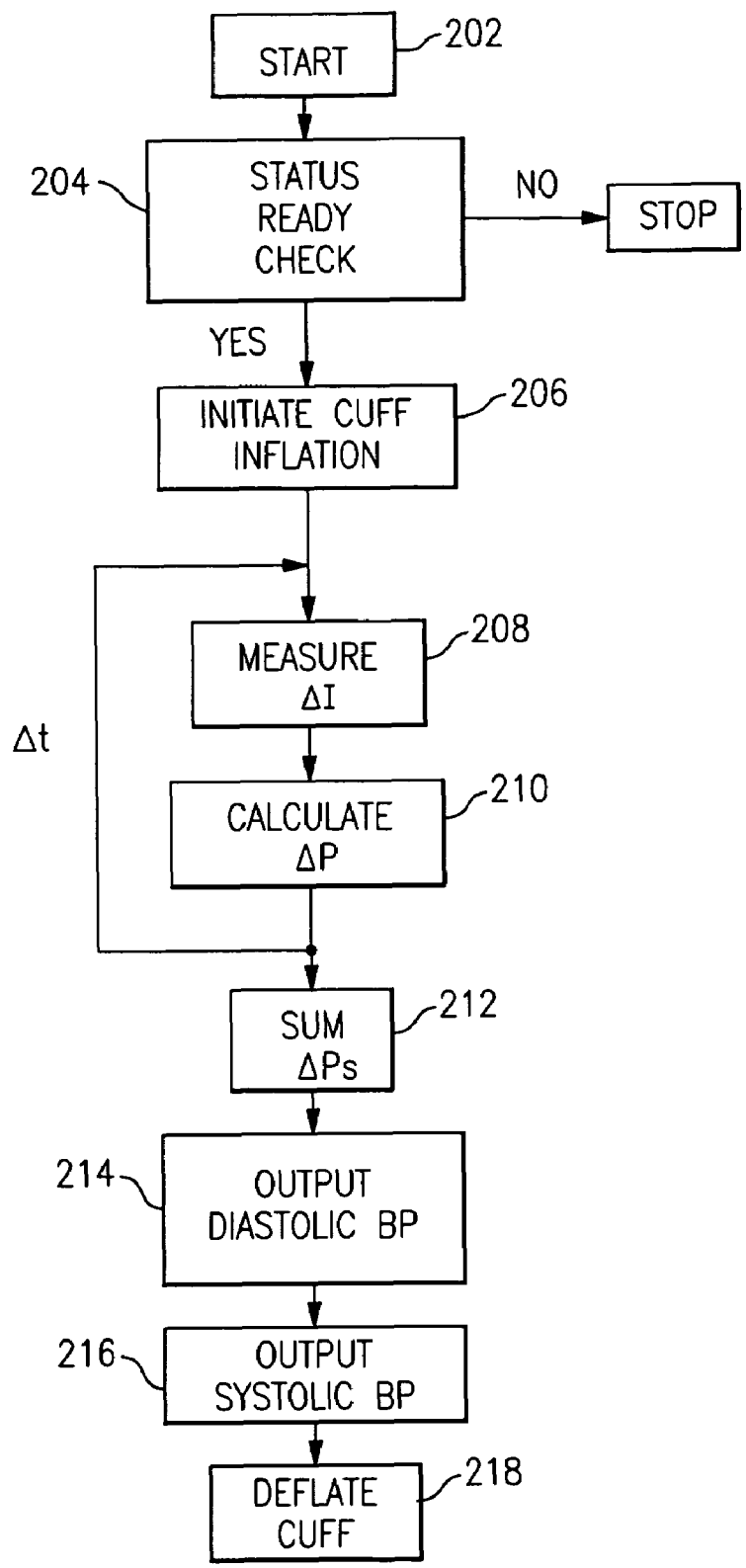
FIG. 3 is a schematic flow diagram that illustrates an exemplary embodiment of the steps in a method of determining blood pressure in accordance with the invention.

An exemplary embodiment of the steps of the method of the invention for determining blood pressure is illustrated schematically by the flow diagram depicted in FIG. 3. The process starts at step 202, labeled "Start", that represents initiation of the of the blood pressure measurement process, including at step 204 all necessary internal initiation routines within the microprocessor 32 and the NIPB module 34 to confirm a ready status for the apparatus 10, as well as thereafter initiating at step 206, if the ready status is verified, the process of inflating the blood pressure cuff 100. If the status ready check at step 204 if negative, the process is stopped. In order to commence a measurement of the blood pressure of an individual, the operator places an inflatable cuff 100, appropriate in size for the individual, at an appropriate location about a limb, such as an arm of the individual, presses the on/off button 21 to power up the apparatus 10, confirms that the apparatus is properly made ready, and then presses the start button 23 to initiate the cuff inflation process.

Upon receipt of a start signal upon depression of the start button 23, the controller 30 opens the supply of current from the power supply 70 through line 72 to the DC motor 60 for energizing the motor 60 to drive the pump 50 to pump a pressurizing fluid, most commonly air, through the tube 35 to the cuff 100, thereby initiating inflation of the cuff. At this point, the NIPB module 34 of the controller 30 also initiates the process of determining the incremental change in cuff pressure over a very small time increment, $\Delta t$, selected to be within the range of about $\frac{1}{200}^{th}$ to about $\frac{1}{100}^{th}$ of a second. At step 208, the NIBP 34, which is in electrical signal communication with the motor current monitor 40 via line 45, repeatedly queries the motor current monitor 40 at intervals equal to the selected time increment and in reply receives a signal indicative of the current drawn by the motor 60 at that instant in time. The NIBP module 34 then, at step 210, calculates the incremental pressure change over that time increment based on the measured incremental current change via the relationship hereinbefore specified. The NIPB module 34 repeats steps 208 and 210 for each incremental increase, $\Delta t$, in time throughout the cuff inflation period.

At step 212, the NIPB module 34 keeps a running sum of the incremental pressure changes from initiation through completion of the cuff inflation process, updating the sum at every $\Delta t$. In this manner, the pressure with the cuff 100 is known by the NIBP module at any point in the cuff inflation process. The NIBP module 34 simultaneously uses conventional techniques, such as, for example, auscultatory methods or oscillometric methods, to monitor arterial blood pressure sounds to indicate when the systolic and diastolic blood pressures have been reached. Knowing the cuff pressure in real time via the method of the invention described hereinbefore, when the NIPB module 34 determines that the diastolic blood pressure of the subject is reached, the NIPB module 34 records the corresponding cuff pressure value and reports that cuff pressure to the microprocessor 32 as the diastolic pressure at step 214. Similarly, when the NIPB module 34 determines that the diastolic blood pressure of the subject is reached, the NIPB module 34 records the corresponding cuff pressure value and reports that cuff pressure to the microprocessor 32 as the systolic pressure at step 216. The microprocessor 32 may display the diastolic and systolic blood pressures on the display 20 and may store these blood pressures for later retrieval or downloading to another data storage device. Once the systolic blood pressure has been reported, the NIPB 218 stops inflation of the cuff 100 and initiates deflation of the cuff 100 at step 218 by opening the vent valve 80 to directly vent the cuff 100 through tube 35 to atmosphere.

Persons possessing ordinary skill in the art will recognize that many functions and operations described herein can be implemented in hardware (for example, hard-wired logic), in software (for example, logic encoded in a program operating on a general purpose processor), and in firmware (for example, logic encoded in a non-volatile memory that is invoked for operation of a processor as required). The present invention contemplates the substitution of one implementation of hardware, software and firmware for another implementation of the equivalent functionality using a different one of hardware, software, firmware and any combination thereof.

The present invention has been particularly shown and described with reference to the preferred mode as illustrated in the drawing, it will be understood by one skilled in the art that various changes in detail may be effected therein without departing from the spirit and scope of the invention as defined by the claims.

We claim:

1. A method for determining blood pressure of a vertebrate comprising the steps of:

using an inflatable blood pressure cuff disposed about a limb of the vertebrate, said cuff including a pump driven by a motor;

inflating said cuff for purposes of taking a blood pressure measurement; and calculating the air pressure within said cuff as a function of the torque on the motor at any given time during said inflation step wherein said calculated air pressure measurements provide blood pressure values of the vertebrate in the absence of a pressure transducer.

2. A method as recited in claim 1 wherein the step of determining the air pressure within the cuff as a function of the torque on the motor at any given time during the inflation of the pressure cuff comprises the steps of:

repeatedly calculating the incremental change in pressure in the pressure cuff over a series of small time increments; and summing the calculated incremental pressure changes from the initiation of cuff inflation to a desired point in time during the inflation of the pressure cuff.

3. A method as recited in claim 2 wherein the step of repeatedly calculating the incremental change in pressure in the pressure cuff over a series of small time increments comprises repeatedly calculating the incremental change in pressure in the pressure cuff over a series of equal time increments, the time increment selected to be less than $\frac{1}{40}^{th}$ of second.

4. A method as recited in claim 3 wherein the time increment is selected to be in the range of about $\frac{1}{200}^{th}$ to about $\frac{1}{100}^{th}$ of a second.

5. A method as recited in claim 2 wherein the step of calculating the incremental change in pressure in the pressure cuff comprises calculating the incremental change in pressure in the pressure cuff as a function of the incremental change in current drawn by the pump motor over the time increment.

6. A method as recited in claim 5 wherein the time increment is selected to be less than $1/40^{th}$ of a second.

7. A method as recited in claim 5 wherein the time increment is selected to be in the range of about $1/200^{th}$ to about $1/100^{th}$ of a second.

* * * * *